US008628529B2

(12) United States Patent
Aldridge et al.

(10) Patent No.: US 8,628,529 B2
(45) Date of Patent: Jan. 14, 2014

(54) SURGICAL INSTRUMENT WITH MAGNETIC CLAMPING FORCE

(75) Inventors: Jeffrey L. Aldridge, Lebanon, OH (US); David A. Witt, Maineville, OH (US); Mary E. Mootoo, Cincinnati, OH (US); Zhifan F. Huang, Mason, OH (US); Timothy G. Dietz, Terrace Park, OH (US); Raymond M. Banks, Cupertino, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 623 days.

(21) Appl. No.: 12/911,943

(22) Filed: Oct. 26, 2010

(65) Prior Publication Data

US 2012/0101488 A1  Apr. 26, 2012

(51) Int. Cl.
*A61B 18/18* (2006.01)

(52) U.S. Cl.
USPC ............... 606/52; 606/51; 606/206; 606/207; 606/208

(58) Field of Classification Search
USPC ................................ 606/33, 51, 52, 206–208
See application file for complete search history.

(56) References Cited

U.S. PATENT DOCUMENTS

| 2,366,274 A | 1/1945 | Luth et al. |
| 2,458,152 A | 1/1949 | Eakins |
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |

(Continued)

FOREIGN PATENT DOCUMENTS

| DE | 29623113 U1 | 10/1997 |
| DE | 20004812 U1 | 9/2000 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Linda Dvorak
*Assistant Examiner* — Khadijeh Vahdat

(57) ABSTRACT

A surgical instrument comprising an end effector, the end effector comprising first and second opposing jaw members, wherein at least one of the first and second jaw members are moveable such that the first and second jaw members are transitionable between open and closed positions. The first jaw member may comprise a permanent magnet. The second jaw member may also comprise a magnet (e.g., permanent or soft). The magnetic motive force between the magnets of the first and second jaw members may attract each other to thereby reduce the external force required to transition the first and second jaw members to the closed position. In addition, the magnets may be configured to repeal each other to thereby aid in opening the jaw members.

12 Claims, 7 Drawing Sheets

(56) References Cited

U.S. PATENT DOCUMENTS

Figure 1:
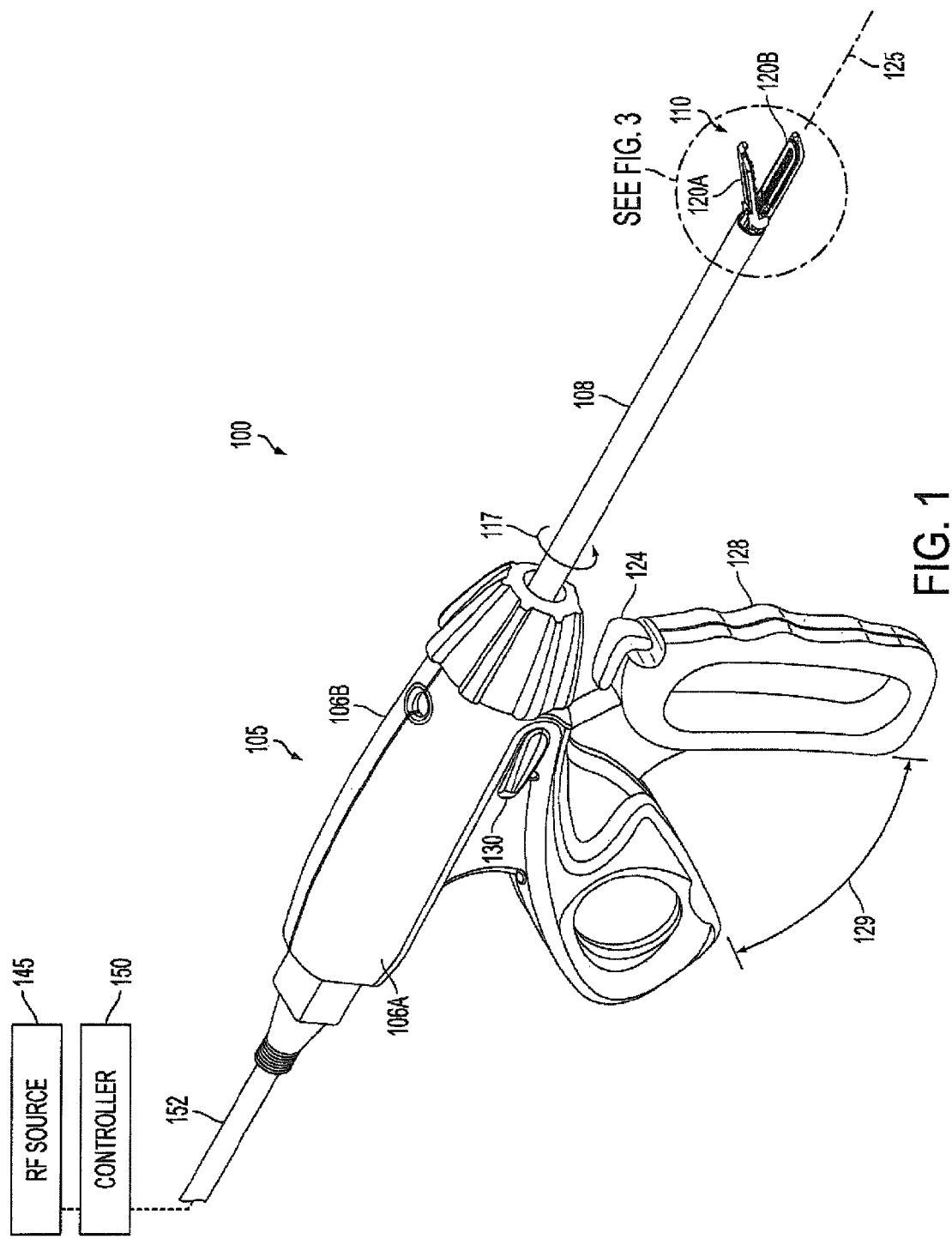

| Patent Number | Date | Inventor |
|---|---|---|
| 4,545,926 A | 10/1985 | Fouts, Jr. et al. |
| 4,550,870 A | 11/1985 | Krumme et al. |
| 4,582,236 A | 4/1986 | Hirose |
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,190,541 A | 3/1993 | Abele et al. |
| 5,205,459 A | 4/1993 | Brinkerhoff et al. |
| 5,285,945 A | 2/1994 | Brinkerhoff et al. |
| 5,309,927 A | 5/1994 | Welch |
| 5,318,589 A | 6/1994 | Lichtman |
| 5,339,723 A | 8/1994 | Huitema |
| 5,361,583 A | 11/1994 | Huitema |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,429,131 A * | 7/1995 | Scheinman et al. .......... 600/374 |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,618,307 A | 4/1997 | Donlon et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,782,834 A | 7/1998 | Lucey et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,876,401 A | 3/1999 | Schulze et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,483 A | 8/2000 | Palmer et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,055,731 B2 | 6/2006 | Shelton, IV et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,252,667 B2 | 8/2007 | Moses et al. |
| 7,267,685 B2 | 9/2007 | Butaric et al. |
| 7,287,682 B1 | 10/2007 | Ezzat et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,491,201 B2 | 2/2009 | Shields et al. |
| 7,510,107 B2 | 3/2009 | Timm et al. |
| 7,513,025 B2 | 4/2009 | Fischer |
| 7,517,349 B2 | 4/2009 | Truckai et al. |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,645,277 B2 | 1/2010 | McClurken et al. |
| 7,658,311 B2 | 2/2010 | Boudreaux |

(56) References Cited

U.S. PATENT DOCUMENTS

| | | | |
|---|---|---|---|
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,020,743 B2 | 9/2011 | Shelton, IV |
| 8,070,036 B1 | 12/2011 | Knodel et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,277,446 B2 | 10/2012 | Heard |
| 8,282,669 B2 | 10/2012 | Gerber et al. |
| 8,298,232 B2 | 10/2012 | Unger |
| 8,323,310 B2 | 12/2012 | Kingsley |
| 2002/0165541 A1 | 11/2002 | Whitman |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0143260 A1* | 7/2004 | Francischelli ............ 606/41 |
| 2004/0193150 A1 | 9/2004 | Sharkey et al. |
| 2004/0232196 A1 | 11/2004 | Shelton, IV et al. |
| 2004/0260273 A1* | 12/2004 | Wan ........................ 606/1 |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173813 A1 | 7/2007 | Odom |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1* | 10/2007 | Paden et al. ............ 324/228 |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0071271 A1* | 3/2008 | Francischelli ............ 606/51 |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0138003 A1 | 5/2009 | Deville et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2009/0326530 A1 | 12/2009 | Orban, III et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0301605 A1 | 12/2011 | Horner |
| 2011/0306963 A1 | 12/2011 | Dietz et al. |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0136353 A1 | 5/2012 | Romero |
| 2012/0150176 A1 | 6/2012 | Weizman |
| 2013/0023875 A1 | 1/2013 | Harris et al. |
| 2013/0053831 A1 | 2/2013 | Johnson et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |

(56) References Cited

FOREIGN PATENT DOCUMENTS

| | | |
|---|---|---|
| EP | 0640317 B1 | 9/1999 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| WO | WO 93/22973 A1 | 11/1993 |
| WO | WO 96/35382 A1 | 11/1996 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |
| WO | WO 01/28444 A1 | 4/2001 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/089717 A1 | 7/2011 |

OTHER PUBLICATIONS

Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, Engineering Formulas § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, Integrated Circuit Engineering, Addison-Wesley Publishing, Reading, MA (1979). (book—not attached).
U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/797,207, filed Jun. 9, 2010.
U.S. Appl. No. 12/797,252, filed Jun. 9, 2010.
U.S. Appl. No. 12/797,288, filed Jun. 9, 2010.
U.S. Appl. No. 12/797,305, filed Jun. 9, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.

(56) References Cited

OTHER PUBLICATIONS

U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
International Search Report for PCT/US2011/057705, Jan. 17, 2012 (4 pages).
Wright, et al., "Time-Temperature Equivalence of Heat-Induced Changes in Cells and Proteins," Feb. 1998. ASME Journal of Biomechanical Engineering, vol. 120, pp. 22-26.
U.S. Appl. No. 13/221,410, filed Aug. 30, 2011.
U.S. Appl. No. 13/189,169, filed Jul. 22, 2011.
U.S. Appl. No. 12/647,134, filed Dec. 24, 2009.

* cited by examiner (Closed)

(Open)

SURGICAL INSTRUMENT WITH MAGNETIC CLAMPING FORCE

BACKGROUND

Many surgical devices comprise end effectors with opposing jaw members that are capable of opening and closing. The jaw members grip tissue therebetween when the jaw members are in the closed position. Many such devices are hand-powered, whereby the operator retracts a closure trigger to cause the jaw members to transition to the closed positions, and releases the closure trigger to cause the jaw members to transition to the open position. Other types of surgical devices use electrical or pneumatic motors to close the jaw members.

Ways to reduce the external force required to clamp the jaw members or to make the required clamping force more uniform are desired.

SUMMARY

In one general aspect, the present invention is directed to a surgical instrument comprising an end effector, the end effector comprising first and second opposing jaw members, wherein at least one of the first and second jaw members are moveable such that the first and second jaw members are transitionable between open and closed positions. The first jaw member may comprise a permanent magnet. The second jaw member may also comprise a magnet (e.g., permanent or soft). The magnetic motive force between the magnets of the first and second jaw members may attract each other to thereby reduce the external force required to transition the first and second jaw members to the closed position. In addition, the magnets may be configured to repeal each other to thereby aid in opening the jaw members.

FIGURES

Figure 4:
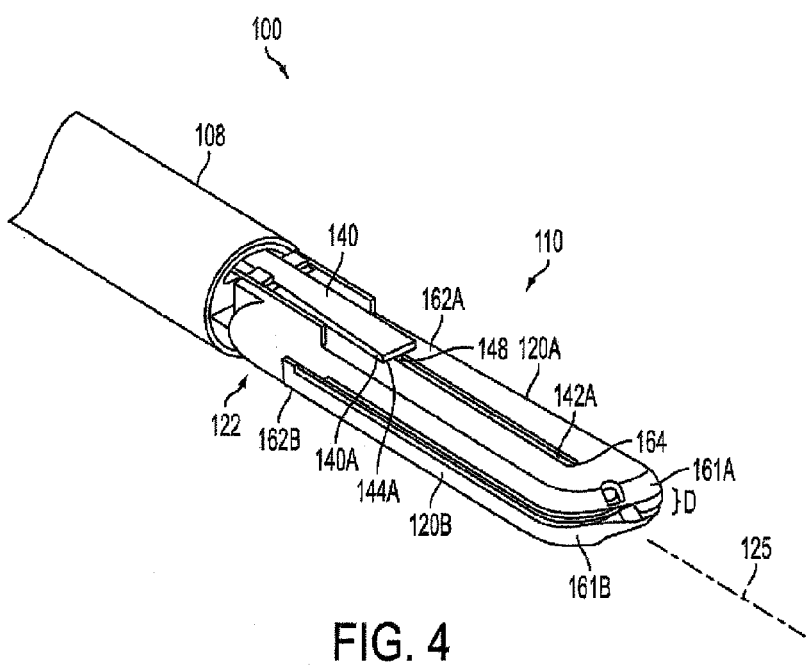
Figure 5:
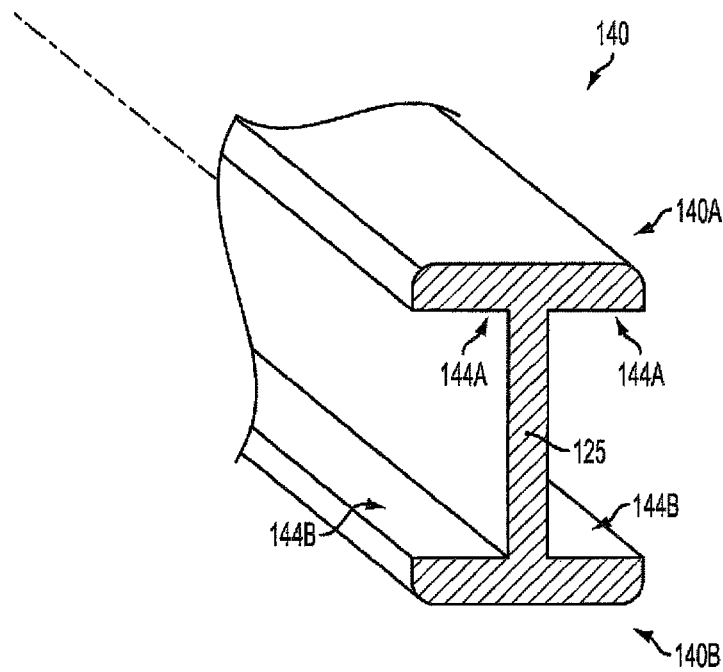
Figure 6A:
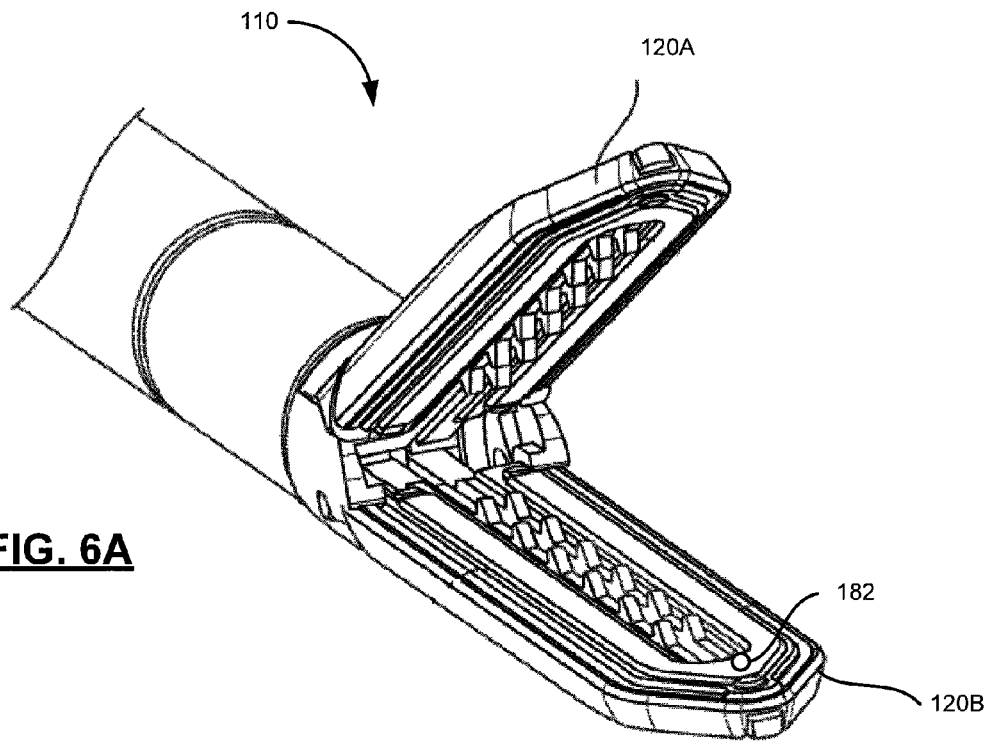
Figure 6B:
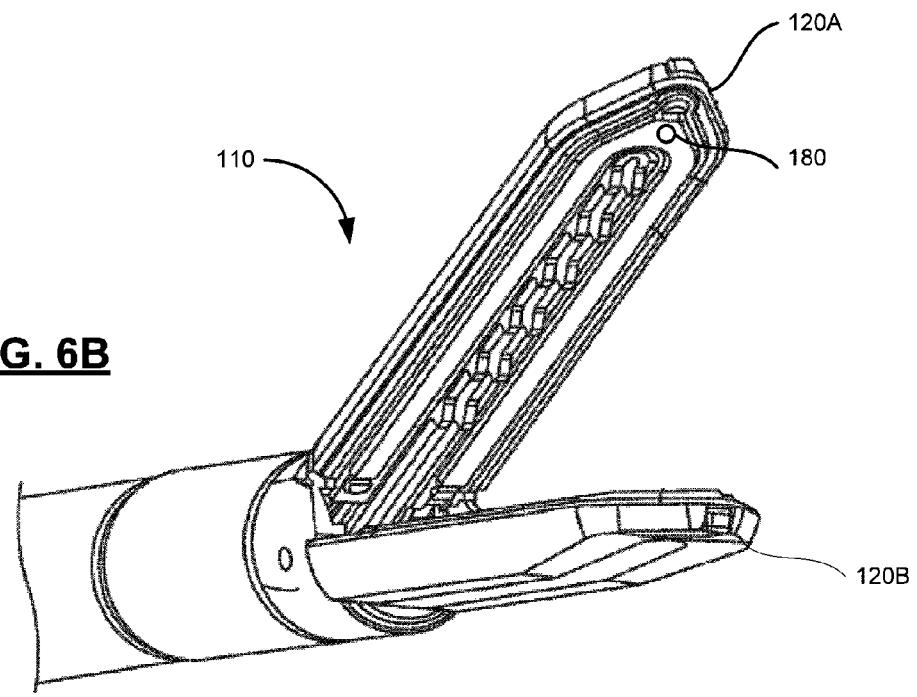
Figures 7A, 7B:
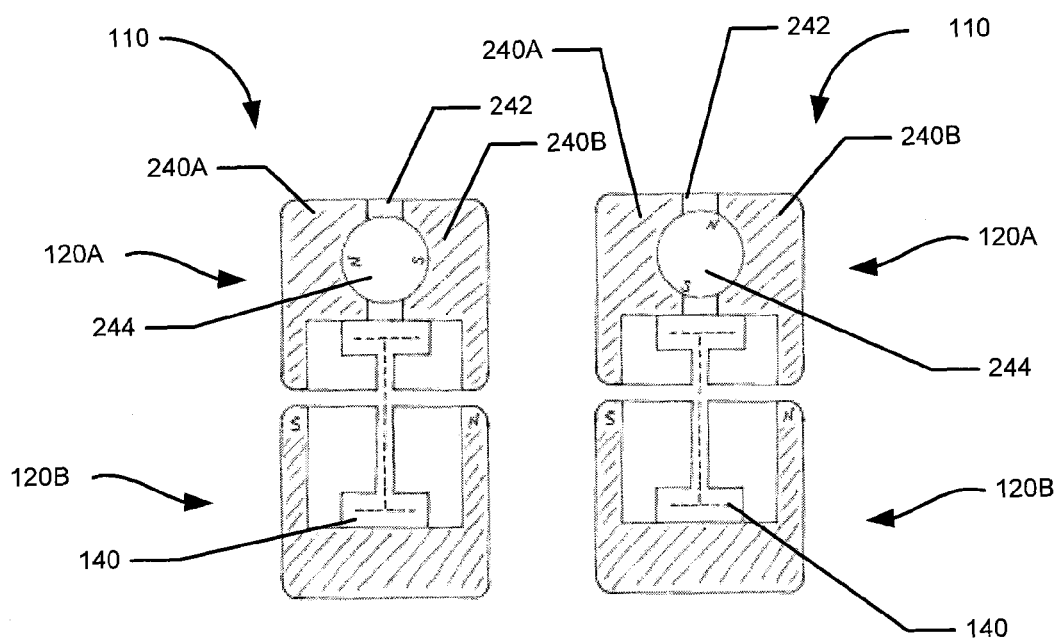
Figure 8:
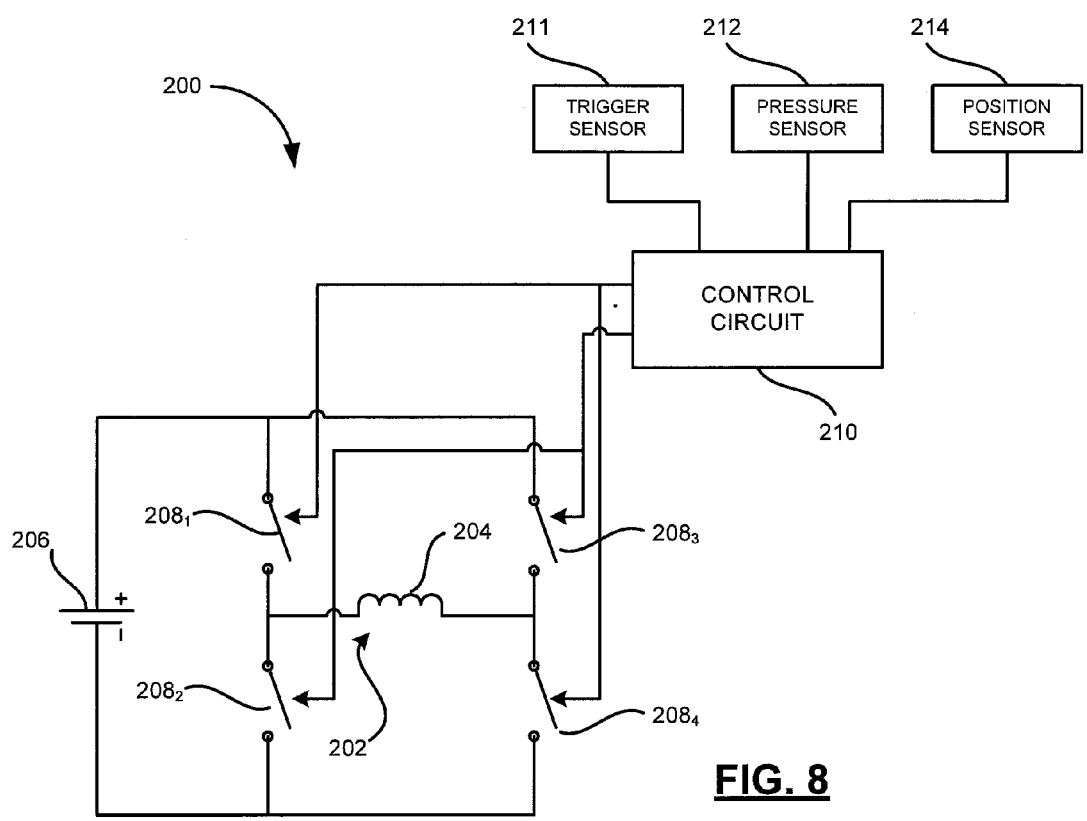

Various embodiments of the present invention are described herein by way of example in conjunction with the following figures, wherein:

FIGS. 1-5 illustrate one type of surgical device that may implement embodiments of the present invention;

FIGS. 6A-B illustrate opposing jaw members of the surgical device of FIGS. 1-5 according to various embodiments of the present invention;

FIGS. 7A-B illustrate opposing jaw members of the surgical device of FIGS. 1-5 according to various embodiments of the present invention; and FIG. 8 is a diagram of a circuit comprising an electromagnet according to various embodiments of the present invention.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

In one general aspect, the present invention is directed to any type of surgical device having an end effector with at least two jaw members for gripping or positioning tissue therebetween, and that uses magnetic motive force between magnets in the respective jaw members to aid in clamping and/or opening the jaw members. FIGS. 1-5 illustrate one type of surgical device 100 that may implement embodiments of the present invention. The illustrated device 100 is configured for transecting captured tissue positioned between the jaw members and for contemporaneously welding the captured tissue margins with controlled application of RF energy. Although the device 100 uses RF energy to weld the tissue margins, the present invention is not so limited and other mechanisms could be used for clamping the tissue in other embodiments, such as staples, harmonics, adhesives, etc. In addition, embodiments of the present invention could be used in a clamping device, such as various types of hemostats or other types of grippers. As shown in the example of FIGS. 1-5, the device 100 can comprise a proximal handle 105, a distal working end or end effector 110, and an introducer or elongate shaft 108 disposed in-between. End effector 110 may comprise a set of openable-closeable jaw members with straight or curved jaws: an upper first jaw 120A and a lower second jaw 120B. In various embodiments, first jaw 120A and second jaw 120B may each comprise an elongate slot or channel 142A and 142B (see FIG. 3), respectively, disposed outwardly along their respective middle portions. First jaw 120A and second jaw 120B may be coupled to an electrical source or RF source 145 and a controller 150 through electrical leads in cable 152. Controller 150 may be used to activate electrical source 145.

Figure 2:
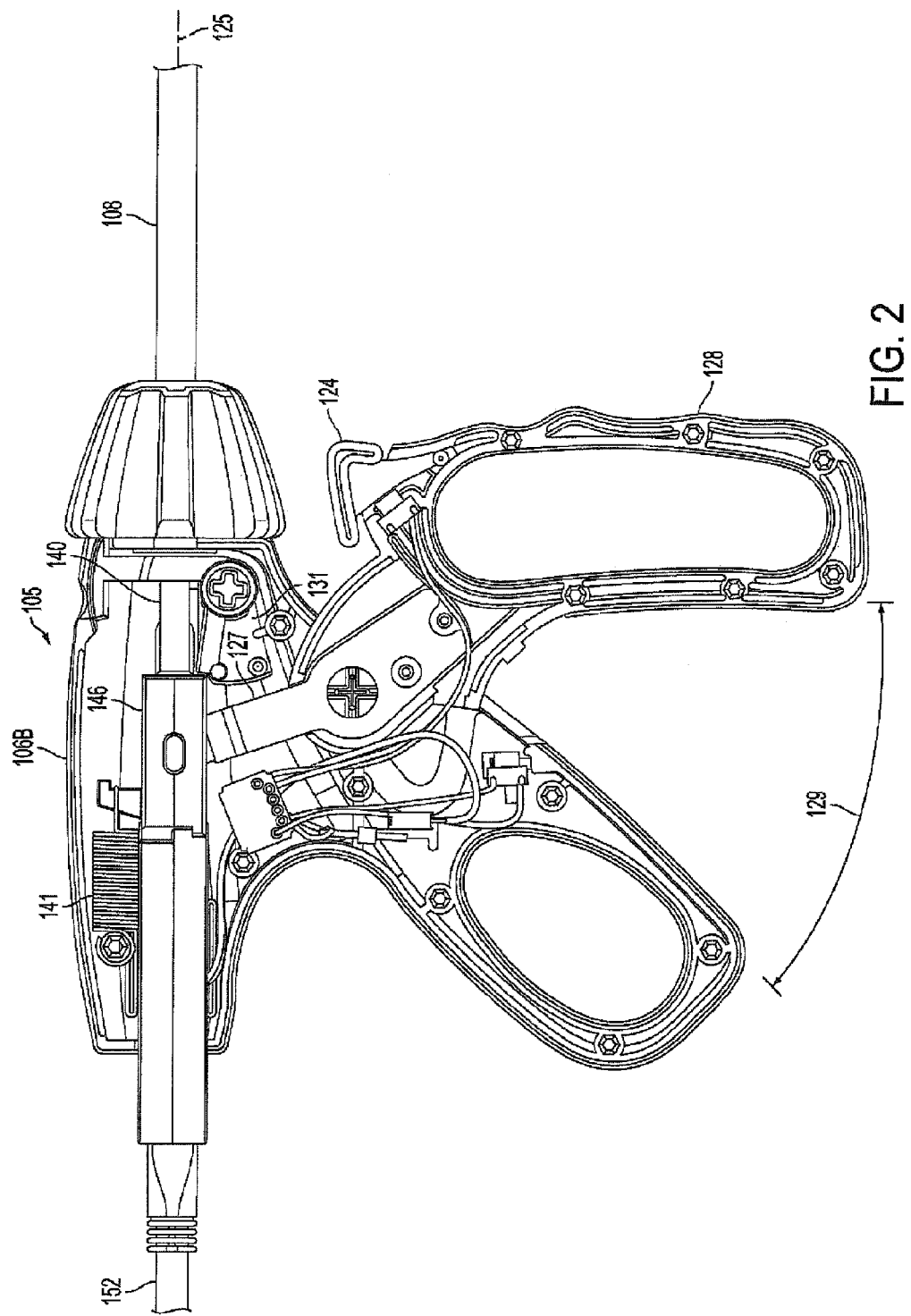

FIG. 2 is a side view of the handle 105 of device 100, shown with half of a first handle body 106A (see FIG. 1) removed to illustrate some of the components within second handle body 106B. Handle 105 may comprise a lever arm 128 that may be pulled along a path 129. Lever arm 128 may be coupled to a movable cutting member 140 disposed within elongate shaft 108 by a shuttle 146 operably engaged to an extension 127 of lever arm 128. The shuttle 146 may further be connected to a biasing device, such as spring 141, which may also be connected to the second handle body 106B, to bias the shuttle 146 and thus the cutting member 140 in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers, or sliders for actuating the first jaw 120A and second jaw 120B. Elongate shaft 108 may have a cylindrical or rectangular cross-section and can comprise a thin-wall tubular sleeve that extends from handle 105. Elongate shaft 108 may include a bore extending therethrough for carrying actuator mechanisms, for example, cutting member 140, for actuating the jaws and for carrying electrical leads for delivery of electrical energy to electrosurgical components of end effector 110.

End effector 110 may be adapted for capturing (or clamping), welding, and transecting tissue in various embodiments. First jaw 120A and second jaw 120B may close to thereby capture, clamp, or engage tissue about a longitudinal axis 125 defined by cutting member 140. First jaw 120A and second jaw 120B may also apply compression to the tissue. Elongate shaft 108, along with first jaw 120A and second jaw 120B, can be rotated a full 360° degrees, as shown by arrow 117, relative to handle 105 through, for example, a rotary triple contact. First jaw 120A and second jaw 120B can remain openable and/or closeable while rotated.

Figure 3:
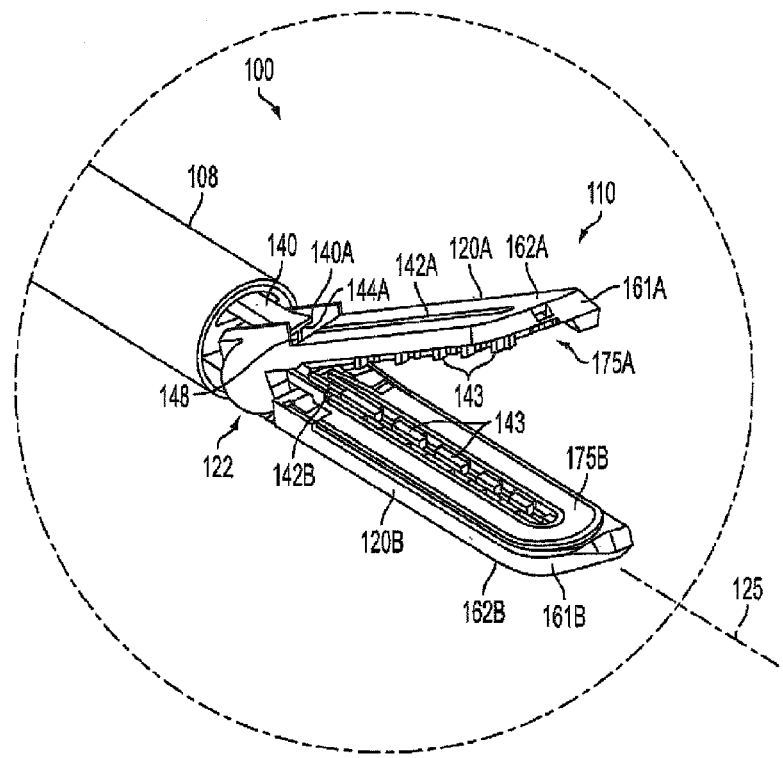

The jaw members of the end effector 110 are transitionable between open and closed positions, as shown in FIGS. 3 and 4, which are perspective views of end effector 110 in the open and closed positions, respectively. In various embodiments, the first jaw 120A and second jaw 120B may each have tissue-gripping elements, such as teeth 143, disposed on the inner portions of first jaw 120A and second jaw 120B. First jaw 120A may comprise an upper first jaw body 161A with an upper first outward-facing surface 162A and an upper first energy delivery surface 175A. Second jaw 120B may comprise a lower second jaw body 161B with a lower second outward-facing surface 162B and a lower second energy delivery surface 175B. First energy delivery surface 175A and second energy delivery surface 175B may both extend in a "U" shape about the distal end of end effector 110.

Referring briefly now to FIG. 5, a portion of cutting member 140 is shown. The lever arm 128 of handle 105 (see FIG. 2) may be adapted to actuate cutting member 140, which also functions as a jaw-closing mechanism. For example, cutting member 140 may be urged distally as lever arm 128 is pulled proximally along path 129 via shuttle 146, seen in FIG. 2 and discussed above. The cutting member 140 may comprise one or several pieces, but in any event, may be movable or translatable with respect to the elongate shaft 108 and/or jaws 120A, 120B. In addition, in at least one embodiment, the cutting member 140 may be made of 17-4 precipitation hardened stainless steel. The distal end of cutting member 140 may comprise a flanged "I"-beam configured to slide within channels 142A and 142B in jaws 120A and 120B. Cutting member 140 may slide within channels 142A, 142B to open and close first jaw 120A and second jaw 120B. The distal end of cutting member 140 may also comprise upper flange or "c"-shaped portion 140A and lower flange or "c"-shaped portion 140B. The flanges 140A and 140B respectively define inner cam surfaces 144A and 144B for engaging outward facing surfaces of first jaw 120A and second jaw 120B. The opening-closing of jaws 120A and 120B can apply very high compressive forces on tissue using cam mechanisms which may include reciprocating "I-beam" cutting member 140 and the outward facing surfaces 162A, 162B of jaws 120A, 120B.

More specifically, referring now to FIGS. 3-5, collectively, inner cam surfaces 144A and 144B of the distal end of cutting member 140 may be adapted to slidably engage first outward-facing surface 162A and second outward-facing surface 162B of first jaw 120A and second jaw 120B, respectively. Channel 142A within first jaw 120A and channel 142B within second jaw 120B may be sized and configured to accommodate the movement of cutting member 140, which may comprise a tissue-cutting element, for example, a sharp distal edge. FIG. 4, for example, shows the distal end of cutting member 140 advanced at least partially through channels 142A and 142B (see FIG. 3). The advancement of cutting member 140 can close end effector 110 from the open configuration shown in FIG. 3. In the closed position shown by FIG. 4, upper first jaw 120A and lower second jaw 120B define a gap or dimension D between the first energy delivery surface 175A and second energy delivery surface 175B of first jaw 120A and second jaw 120B, respectively. Dimension D equals from about 0.0005" to about 0.005" and preferably between about 0.001" to about 0.002". In addition, the edges of first energy delivery surface 175A and second energy delivery surface 175B may be rounded to prevent the dissection of tissue.

Referring now to FIGS. 1 and 3, end effector 110 may be coupled to electrical source 145 and controller 150. First energy delivery surface 175A and second energy delivery surface 175B may likewise each be coupled to electrical source 145 and controller 150. First energy delivery surface 175A and second energy delivery surface 175B may be configured to contact tissue and delivery electrosurgical energy to engaged tissue, which is adapted to seal or weld the tissue. Controller 150 can regulate the electrical energy delivered by electrical source 145, which in turn delivers electrosurgical energy to first energy-delivery surface 175A and second energy-delivery surface 175B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. Further, the opposing first and second energy delivery surfaces 175A and 175B may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,354,440; 7,381,209; 7,311,709; 7,309,849; 7,220,951; 7,189,233; 7,186,253; 7,169,156; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

In at least one embodiment, one or both of the jaws 120A, 120B may be flexible, such that one of the jaws is configured to flex when gripping tissue. In at least one embodiment, referring now to FIGS. 3 and 4, the surgical instrument 100 may comprise elongate shaft 108 and end effector 110, which may be coupled together as described above. The end effector may further comprise first jaw 120A, second jaw 120B, and cutting member 140. The first jaw 120A, as will be discussed below, may be flexible. Further, the first and second jaws 120A and 120B may be pivotably coupled together at hinge portion 122. The first flexible jaw 120A may also define channel 142A. The cutting member 140 may be sized and configured to fit at least partially within the channel 142A. The cutting member 140 may also be configured to translate along the channel 142A, as described above, between a retracted position and a fully advanced position. The retracted position can be seen in FIG. 3, where the jaws 120A, 120B are in an open position and a distal end 148 of the cutting member 140 is positioned proximal to the upper outward-facing surface 162A. The fully advanced position, while not shown, occurs when the distal end 148 of the cutting member 140 is advanced to a distal end 164 of channel 142A and the jaws are in a closed position, see FIG. 4.

The end effector 110 may further include at least one compression element extending from the cutting member 140, such as inner cam surface 144A and/or 144B of flanges 140A and 140B, see FIG. 5. Further, as described above, the compression element(s), or cam surfaces 144A and/or 144B, may be configured to cause the first flexible jaw 120A to rotate with respect to the second jaw 120B from the open position (see FIG. 3) to a closed position (see FIG. 4) when the cutting member 140 translates with respect to the first flexible jaw 120A beyond the retracted position. For example, FIG. 4, as mentioned above, shows the distal end 148 of the cutting member 140 in a partially advanced position, that is, beyond the retracted position seen in FIG. 3, but before the fully advanced position, described above. As seen in FIG. 4, the compression element(s), or inner cam surface 144A of flange 140A, extending from the cutting member 140, are in contact with the upper outward-facing surface 162A, see FIG. 5, for example, thereby holding the first flexible jaw 120A in the closed position as seen in FIG. 4.

As discussed above, embodiments of the present invention use magnetomotive force between magnets in the respective jaw members of the end effector, such as first jaw 120A and second jaw 120B of end effector 110, to aid in clamping and/or opening the jaw members 120A-120B. When there is an attractive magnetomotive force between the magnets in the respective jaw members, the magnetomotive force may aid in clamping the jaw members, thereby reducing the external force-to-fire (FTF) required to clamp the end effector. In such embodiments, the end effector 110 may comprise other force means for overcoming the attractive magnetomotive force when attempting to open the jaw members 120A, 120B, such as, for example, a spring biased to urge the jaw members 120A, 120B apart. When there is a repellant magnetomotive force between the magnets in the respective jaw members, the magnetomotive force may aid in opening or unclamping the jaw members.

FIGS. 6A-B show the jaws 120A, 120B having respective magnets 180, 182. The magnets 180, 182 are preferably located at or toward the distal ends of the jaws 120A, 120B, although in other embodiments the magnets 180, 182 may not be located at the distal end of the jaws 120A, 120B, such as more proximate locations in the jaw members 120A, 120B. In addition, the magnets 180, 182 are preferably aligned, such as both at the distal end of the end effector, so that when the jaw members 120A, 120B are in the closed position, the magnets 180, 182 are in close proximity. Additionally, although only one magnet 180 is shown in first jaw 120A and only one corresponding magnet 182 is shown in second jaw 120B, multiple aligned, corresponding magnets pairs may be used in the first and second jaws 120A, 120B to increase the magnetomotive force between the jaws 120A, 120B.

In various embodiments, at least one of the magnets, such as magnet 180 in first jaw 120A, may be a permanent magnet. As such, the permanent magnet 180 may comprise permanent magnetic material, such as iron, nickel, cobalt, magnetic rare earth metals (such as neodymium and samarium), and/or magnetic alloys thereof (e.g., Alnico, neodymium-iron-boron, or samarium-cobalt). In addition, the permanent magnet 180 may be a switchable permanent magnet, such as an electromagnet or a rotatable permanent magnet, described further below.

The magnet 182 of the second jaw 120B may be, for example, a permanent magnet or a soft magnet. In embodiments where the magnet 182 is a permanent magnet, it may comprise permanent magnetic material (such as the example permanent magnetic materials described above). In addition, in various embodiments, the permanent magnet 182 may comprise a switchable permanent magnet, such as an electromagnet or a rotatable magnet, for example. In embodiments where the magnet 182 is a soft magnet, the magnet 182 may comprise soft ferromagnetic material, such as steel and other nickel-iron or nickel-cobalt alloys. In embodiments where the magnet 182 is a soft magnet, the magnetomotive force between the magnets 180, 182 may only assist in closing the jaw 120A, 120B and not in opening the jaws 120A, 120B as the magnetomotive force is an attractive force only. When both magnets 180, 182 are made of permanent magnetic materials, they may repeal or retract each other, depending on their magnetic polarity. If the permanent magnets 180, 182 are configured to attract each other, their magnetomotive force will aid in closing the jaws 120A, 120B, but hinder opening the jaws 120A, 120B. Conversely, if the permanent magnets 180, 182 are configured to repeal each other, their magnetomotive force will aid in opening the jaws 120A, 120B, but hinder closing the jaws 120A, 120B.

As mentioned above, either the magnet 180 or the magnet 182 may be an electromagnet. In such embodiments, the current through the electromagnet may be switched, or reversed, to reverse the magnetomotive force between the magnets 180,182. That way, depending on the orientation of the magnetic field from the electromagnet(s) (which depends on the direction of the current through the coil of the electromagnet(s)), the electromagnet(s) may be used to assist closing and opening of the jaws 120A, 120B of the end effector. FIG. 8 is a diagram of a circuit 200 for controlling an electromagnet 202 according to various embodiments. The electromagnet 202 may be used for magnet 180 and/or magnet 182, for example. In the illustrated embodiment, the coil 204 of the electromagnet 202 is coupled to a power source 206 via a bridge circuit comprising switches $208_{1-4}$. The switches $208_{1-4}$ may be reverse polarity devices, such as BJTs or MOSFETs, for example. The switches $208_{1-4}$ may be discrete devices or they may be part of an integrated circuit, for example. The switches $208_{1-4}$ are controlled by a control circuit 210, which controls opening and closing of the switches $208_{1-4}$ (e.g., the turning on and turning off of the switches $208_{1-4}$).

In one embodiment, the control circuit 210 controls the switches $208_{1-4}$ such that switches $208_1$ and $208_4$ open and close together, and such that $208_2$ and $208_3$ open and close together, and open and close oppositely from switches $208_1$ and $208_4$. That way, when switches $208_1$ and $208_4$ are closed (on), switches $208_2$ and $208_3$ are open (off), providing a first current direction through the coil 204. When switches $208_2$ and $208_3$ are closed (on), switches $208_1$ and $208_4$ are open (off), providing a second current direction through the coil 204 that is opposite to the first current direction. In that way, the polarity of the magnetic field from the electromagnet 202 can be controlled (e.g., reversed). Preferably, the control circuit 210 controls the switches $208_{1-4}$ such that are not all closed at the same time. The control circuit 210 may be separate from the switches $208_{1-4}$; in other embodiments, the control circuit 210 and the switches $208_{1-4}$ may be part of a common integrated circuit.

In various embodiments, the power source 206 may be remotely located from the electromagnet 202, such as part of the electrical source 145. As such, the electrical source 145 may provide DC power to the circuit 200. Coupling wires through the shaft 108 may couple the remote power source 206 to the switches 208$_{1-4}$ and the electromagnet 202. In other embodiments, the power source 206 may be located in the handle 105. In such embodiments, the power source 206 may comprise one or more battery cells. In a similar manner, the battery cell(s) may be coupled to the switches 208$_{1-4}$ and the electromagnet 202 by wires running through the shaft 108. More details regarding surgical devices having an opening-and-closing end effector and with a battery cell(s) in the handle of the device may be found in the following published U.S. patent application, which are incorporated herein by reference in their entirety: Pub. No. 2007/0175960; Pub. No. 2008/0167522; and Pub. No. 2009/0209979.

The control circuit 210 may receive inputs from user controls and/or sensors of the device 100. For example, when the user retracts the trigger arm 128, retraction of the trigger arm 128 may be sensed by a sensor 211, which sensor output is input to the control circuit 210. Based thereon, the control circuit 210 may control the switches 208$_{1-4}$ such that the magnetic field from the electromagnet 202 aids in closing the jaws 120A, 120B. Conversely, when the lever arm 128 transitions from its closed (or retracted) position to its open (or unretracted) position, the control circuit 210 may control the switches 208$_{1-4}$ so that the polarity of the magnetic field from the electromagnet 202 is reversed, thereby aiding in opening the jaws 120A, 120B. In devices 100 where a push-button(s) is used to open and close the end effector 110, the control circuit 210 may be responsive to activation of the push-button(s) for opening and closing the jaws 120A, 120B.

In various embodiments, the control circuit 210 may be responsive to other sensors, such as a pressure sensor 212 and/or a position sensor 214, for example. The pressure sensor 212 may be located in the end effector 110 and may sense the compression force on the tissue between the jaws 120A, 120B. If the compression force exceeds a threshold level as sensed by the pressure sensor 212, the control circuit 210 may open the switches 208$_{1-4}$ to turn off the electromagnet 202. In addition, in such circumstances, the control circuit 210 could control the switches to open the jaw members. The position sensor 214 may sense, for example, the distance between the jaws 120A, 120B, which is indicative of the thickness of the tissue clamped between the jaws. The position sensor 214 may comprise a Hall effect sensor, for example. In various embodiments, if the tissue thickness is less than a threshold level as sensed by the position sensor 214, the control circuit 210 may open the switches 208$_{1-4}$ to turn off the electromagnet 202. In addition, in such circumstances, the control circuit 210 could control the switches to open the jaw members. More details regarding implementation of a pressure (or load) sensor and/or position sensors in an opening-and-closing end effector of a surgical device may be found in U.S. Pub. No. 2006/0212069, U.S. Pub. No. 2009/0076534, and U.S. patent application Ser. No. 12/647,134, which are incorporated herein by reference in their entirety. In various embodiments, the circuit 200 may also comprise passive circuit elements, such as resistors, to dissipate current to the electromagnet 202, to thereby control the magnitude of the current to the electromagnet 202, and hence the strength of the magnetic field from the electromagnet 202.

In various embodiments, one of the magnets (e.g., magnet 180) may be an electromagnet and the other magnet (e.g., magnet 182) may comprise permanent magnetic or soft magnetic materials. Where the second magnet 182 comprises permanent magnetic materials, the electromagnet 180 may repeal or attract the second magnet 182, depending on the polarity of the magnetic field from the electromagnet 180 (which can be controlled by the control circuit). In other embodiments, both magnets 180, 182 may be electromagnets. In such embodiments, by suitably varying the direction of the current through the coils of the electromagnets (which can be controlled by the control circuit), the two electromagnets can be configured to attract or repeal each other, thereby aiding closing and opening of the jaws 120A, 120B.

The electromagnet(s) 180, 182 may be positioned at the distal end of the jaw member(s) 120, 120B. In other embodiments, the electromagnet(s) 180, 182 may be positioned more proximately in the jaw member(s) 120, 120B. In addition, a magnetic field concentrator(s) may be used to concentrate the magnetic field from the electromagnet(s) 180, 182 at a desired location in the end effector 102. That way, for example, the electromagnet(s) 180, 182 does not need to be located in the precise location where the magnetic field is desired. Examples of a magnetic field concentrator can be found in, for example, U.S. Pat. No. 7,513,025, which is incorporated herein by reference.

In addition to electromagnets, another type of switchable permanent magnet that may be used for one of the magnets is a rotatable permanent magnet, as illustrated in FIGS. 7A and 7B. These figures show cross-sectional front views of the jaws 120A, 120B, with the jaws 120A, 120B connected by the I-beam cutting member 140. In the illustrated example, the upper jaw 120A comprises ferromagnetic side portions 240A-B, separated by a non-ferrous middle portion 242. In various embodiments, the ferromagnetic side portions 240A-B may comprise a ferromagnetic material, such as iron and/or alloys thereof. The non-ferrous middle portion 242 may comprise a non-ferromagnetic material, such as brass or aluminum (Al), for example. The upper jaw 120A may define a central bore or opening, in which a central, rotatable, preferably cylindrical, permanent magnet 244 is disposed. The central rotatable permanent magnet 244 may have opposing poles (e.g., North and South poles), and may be rotatable within the bore between an on (or closed) position (see FIG. 7A) and an off (or open) position (see FIG. 7B). The lower jaw 120B may also comprise permanent magnetic material and may include opposing poles (e.g., North and South poles), as shown in FIGS. 7A-7B. When the central rotatable permanent magnet 244 is in the on or closed position, as shown in FIG. 7A, the jaw members 120A, 120B may experience an attractive magnetomotive force, aiding in closing the jaw members 120A, 120B. When the permanent magnet 244 is in the off or open position, as shown in FIG. 7AB, the jaw members 120A, 120B may experience a repellant magnetomotive force, aiding in opening the jaw members 120A, 120B. The attractive and repellant magnetomotive forces may be adjusted in such an embodiment by controlling the amount of rotation of the central rotatable permanent magnet 244, such as by controlling whether the central rotatable permanent magnet 244 is fully or partially open, and/or fully or partially closed. The central rotatable permanent magnet 244 may be rotated by, for example, a push rod or alternating pulling cables extending through the shaft 108. In other embodiments, inner and outer tube arrangements for the shaft 108 may be used to rotate the central rotatable permanent magnet 244. In addition, rotation of the central rotatable permanent magnet 244 may be coupled to the closing mechanism for the end effector 110 in various embodiments. For example, when the closing mechanism is actuated to close the jaw members 120A, 120B of the end effector 110, the central rotatable permanent magnet 244 may correspondingly be rotated to the closed position to aid in closing of the jaw members 120A, 120B of the end effector 110. Conversely, when the closing mechanism is actuated to open the jaw members 120A, 120B of the end effector 110, the central rotatable permanent magnet 244 may correspondingly be rotated to the open position to aid in opening of the jaw members 120A, 120B of the end effector 110.

The above described embodiments may be employed in any suitable surgical device comprising an opening-closing end effector with two jaw members moveable relative to each other, including, but not limited to bipolar RF surgical devices, harmonic devices (e.g., the jaw members may comprise one jaw and one blade in such embodiments), endo-cutters, clamps, etc.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although the various embodiments of the devices have been described herein in connection with certain disclosed embodiments, many modifications, and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
   an end effector comprising:
      a first jaw member comprising a first magnet, wherein the first magnet comprises a first electromagnet; and
      a second jaw member opposing the first jaw member, wherein the second jaw member comprises a second magnet, and wherein at least one of the first and second jaw members are moveable such that the first and second jaw members are transitionable between open and closed positions, and wherein a magnetic motive force between the first and second magnets reduces an external force required to transition the first and second jaw members to the closed position
   a control circuit for controlling the first electromagnet; and
   a position sensor for sensing a distance between the first and second jaw members, wherein the position sensor is in communication with the control circuit, and wherein the control circuit is responsive to the position sensor in controlling the first electromagnet.

2. The surgical instrument of claim 1, wherein the second magnet comprises a soft magnet.

3. The surgical instrument of claim 2, wherein the soft magnet comprises a soft magnetic material selected from a group consisting of steel, nickel-iron alloy, and nickel-cobalt alloy.

4. The surgical instrument of claim 1, wherein the second magnet comprises a second permanent magnet.

5. The surgical instrument of claim 4, wherein the second permanent magnet comprises a permanent magnetic material.

6. The surgical instrument of claim 5, wherein the permanent magnetic material is selected from a group consisting of iron, nickel, cobalt, neodymium, and samarium.

7. The surgical instrument of claim 4, wherein the second permanent magnet comprises a second electromagnet.

8. The surgical instrument of claim 1, wherein the surgical instrument is selected from a group consisting of a RF surgical instrument, a harmonic surgical instrument, an endo-cutter, and a grasper.

9. The surgical instrument of claim 1, further comprising a pressure sensor for sensing a force being applied to tissue positioned between the first and second jaw members, and wherein:
   the pressure sensor is in communication with the control circuit; and
   the control circuit is additionally responsive to the pressure sensor in controlling the first electromagnet.

10. The surgical instrument of claim 9, further comprising:
    a trigger arm; and a trigger sensor for sensing retraction of the trigger arm by a user of the surgical instrument, wherein:
the trigger sensor is in communication with the control circuit; and
the control circuit is additionally responsive to the trigger sensor in controlling the first electromagnet.

11. A surgical instrument comprising:
an end effector comprising:
a first jaw member comprising:
a magnetic side portion; and
a magnetic middle portion that is a switchable permanent magnet having a longitudinal axis, wherein the magnetic middle portion is rotatable about the longitudinal axis independent of rotation by the magnetic side portion; and
a second jaw member opposing the first jaw member, wherein the second jaw member comprises a second magnet that is a permanent magnet, and wherein at least one of the first and second jaw members are moveable relative to each other such that the first and second jaw members are transitionable between open and closed positions, and wherein, attraction and repellent magnetic motive force between the first and second magnets may be adjustable upon rotation of the magnetic middle portion about the longitudinal axis, wherein, upon rotation to a first position independent of rotation by the magnetic side portion of the first magnet, the magnetic motive force between the first and second magnets reduces an external force required to transition the first and second jaw members to the closed position.

12. The surgical instrument of claim 11, wherein:
the magnetic side portion comprises first and second ferromagnetic sidepieces separated by a non-ferrous middle portion;
the magnetic middle portion is rotatable within a bore defined in the first jaw member; and
the magnetic middle portion comprises opposing magnetic poles.

* * * * *